(12) United States Patent
Randall et al.

(10) Patent No.: US 9,827,363 B2
(45) Date of Patent: *Nov. 28, 2017

(54) DIALYSIS SERVICE BOX

(71) Applicant: WD Manor Mechanical Contractors, Inc., Phoenix, AZ (US)

(72) Inventors: Jeff Randall, Glendale, AZ (US); Bryan DeWitt, Mesa, AZ (US); Peter DeWitt, Mesa, AZ (US); Rick Garcia, Glendale, AZ (US); Don Gustafson, Tempe, AZ (US)

(73) Assignee: W.D. Manor Mechanical Contractors, Inc., Phoenix, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/594,355

(22) Filed: May 12, 2017

(65) Prior Publication Data

US 2017/0281844 A1   Oct. 5, 2017

Related U.S. Application Data

(63) Continuation of application No. 14/486,523, filed on Sep. 15, 2014, now Pat. No. 9,724,457, which is a
(Continued)

(51) Int. Cl.
| | | |
|---|---|---|
| *A61M 1/16* | (2006.01) | |
| *A61M 39/22* | (2006.01) | |
| *B01D 61/30* | (2006.01) | |
| *E03B 7/09* | (2006.01) | |
| *E03C 1/10* | (2006.01) | |

(Continued)

(52) U.S. Cl.
CPC .......... *A61M 1/168* (2013.01); *A61M 1/1656* (2013.01); *A61M 1/1664* (2014.02); *B01D 61/30* (2013.01); *E03B 7/095* (2013.01); *E03C 1/021* (2013.01); *E03C 1/04* (2013.01);
(Continued)

(58) Field of Classification Search
CPC .. A61M 1/1664; A61M 1/1656; A61M 1/168; A61M 39/00; Y10T 137/0402; Y10T 137/8593; Y10T 137/2564; B01D 61/20; B01D 61/22; B01D 61/30; E03C 1/296;
(Continued)

(56) References Cited

U.S. PATENT DOCUMENTS

| | | |
|---|---|---|
| 4,646,211 A | 2/1987 | Gallant et al. |
| 5,253,670 A | 10/1993 | Perrott |

(Continued)

*Primary Examiner* — Terry Cecil
(74) *Attorney, Agent, or Firm* — Jennings Strouss & Salmon, PLC; Michael K. Kelly

(57) ABSTRACT

A dialysis service box for centralized control and plumbing arrangement of a dialysis machine is disclosed. The dialysis service box includes a plumbing arrangement having a supply inlet for supplying a fluid to the dialysis machine, a backflow preventer for preventing retrograde flow through the plumbing arrangement, a trap primer for maintaining a trap seal designed to prevent waste gases from flowing into the dialysis service box and a waste connection for allowing waste from the dialysis machine to exit. The dialysis service box can be universally installed to operate, control and adjust any dialysis machine that requires supply connection, waste connection, backflow preventer and trap primer, or any combination of the foregoing.

20 Claims, 5 Drawing Sheets

Related U.S. Application Data continuation-in-part of application No. 13/180,438, filed on Jul. 11, 2011, now Pat. No. 8,834,718.

(60) Provisional application No. 61/363,084, filed on Jul. 9, 2010.

(51) Int. Cl.
*E03C 1/04* (2006.01)
*E03C 1/02* (2006.01)

(52) U.S. Cl.
CPC ........... *E03C 1/10* (2013.01); *Y10T 137/0402* (2015.04); *Y10T 137/2564* (2015.04)

(58) Field of Classification Search
CPC ... E03C 1/021; E03C 1/04; E03C 1/10; E03B 7/095
See application file for complete search history.

(56) References Cited

U.S. PATENT DOCUMENTS

| | | | |
|---|---|---|---|
| 5,591,344 A * | 1/1997 | Kenley | A61L 2/04 210/134 |
| 6,319,399 B1 | 11/2001 | Peterson et al. | |
| 8,460,544 B2 | 6/2013 | Volker | |
| 8,834,718 B2 | 9/2014 | Randall et al. | |
| 2008/0302988 A1 | 12/2008 | Vilendre et al. | |

* cited by examiner

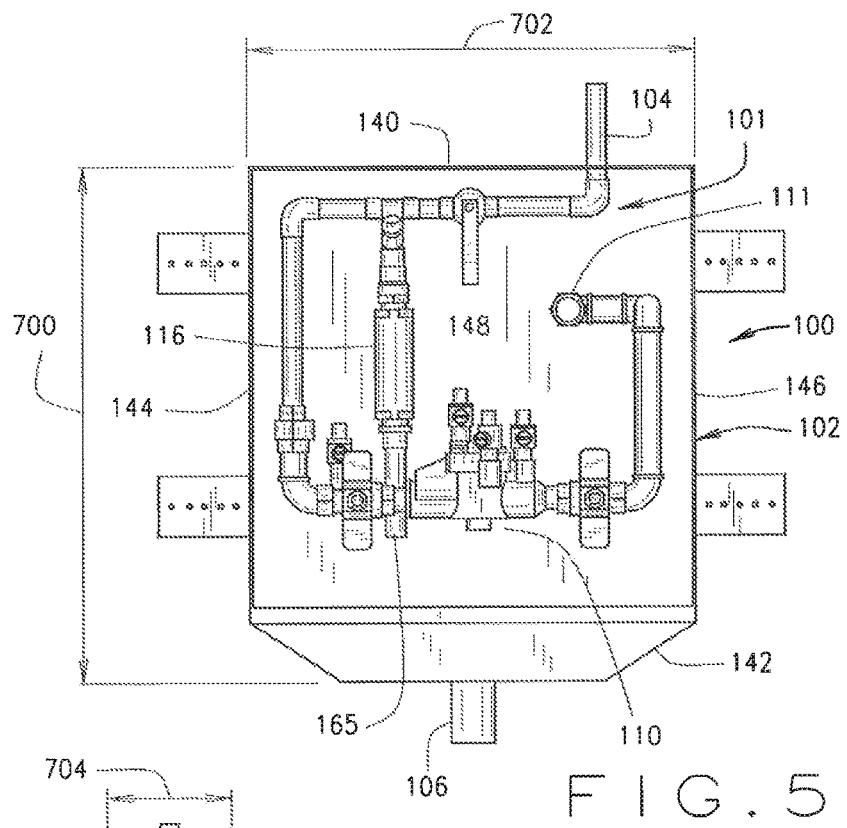
FIG. 5
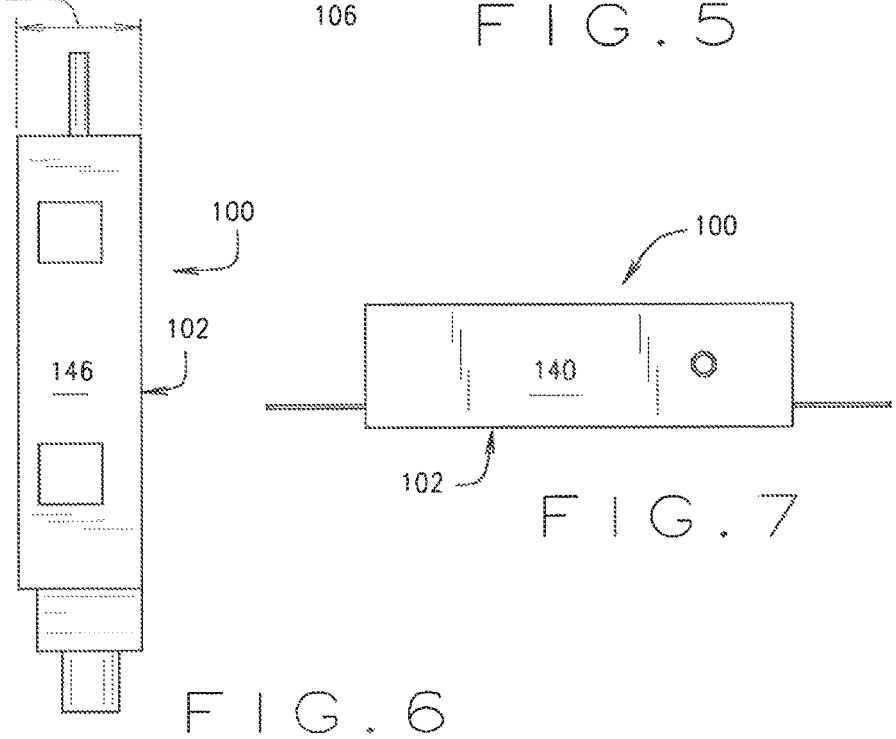
FIG. 6
FIG. 7

DIALYSIS SERVICE BOX

CROSS REFERENCE TO RELATED APPLICATIONS

This application claims priority to co-pending application Ser. No. 14/486,523 filed Sep. 15, 2014, which is a continuation-in-part of application Ser. No. 13/180,438 filed Jul. 11, 2011 (now U.S. Pat. No. 8,834,718 B2) which claims priority to U.S. Provisional Application Ser. No. 61/363,084 filed on Jul. 9, 2010, all of which are hereby incorporated by reference in their entirety.

FIELD

The present disclosure relates to dialysis service box, and in particular to a dialysis service box for providing a centralized compact plumbing connection service box for one or more medical dialysis machines.

BACKGROUND

The dialysis process and procedure is performed by medical care providers in a hospital or other healthcare facility in which an individual to be treated undergoes a process for removing waste and excess water from the blood, and is primarily used to provide an artificial replacement for lost kidney function in individuals with renal failure. In almost all cases the medical care provider utilizes a dialysis machine in which the plumbing connection to the dialysis machine typically requires potable, untreated city tap water for supply to the dialysis machine and a waste drain for receiving waste from the dialysis machine as the individual undergoes treatment. As shown in FIG. 1, a prior art dialysis service system 10 for performing dialysis requires a single service box with a hose bib and drain connection 14 for supplying a water source and removing waste from the dialysis machine. In addition, the prior art hose bib and drain connection 14, in some jurisdictions (consult your local code), requires a backflow preventer 18 for preventing retrograde flow of contaminated water and trap primer 16 for insuring periodic priming of the waste outlet to prevent the backflow of waste gases. As shown, the backflow preventer 18 and the trap primer 16 are located at remote and separate locations relative to the hose bib and drain connection 14, therefore requiring extensive plumbing be installed to interconnect all of the components of the prior art dialysis service system 10.

With the backflow preventer 18 and the trap primer 16 at separate remote locations, numerous drawbacks exist in the current configuration of the prior art dialysis service system 10 which requires multiple dialysis services system locations. This arrangement necessarily increases response time by medical personnel to react to any emergency between multiple locations. In addition, there is the inconvenience and cost in interior design and installation of the plumbing infrastructure that increases the expense to install separate components as well as an increased cost in maintenance and operation in that the existing designs require more wall space, material, labor, and time to install and operate the necessary additional plumbing 12 that must run between all of the remote components of the prior art dialysis system 10. Therefore, there is a need in the art for a dialysis service box that addresses these deficiencies in the prior art dialysis service system 10.

SUMMARY

In one embodiment, a dialysis service box may include a casing having a top side portion, a bottom side portion, a rear side portion, a left side portion and a right side portion that collectively define an enclosure. A water supply inlet is attached to the casing and is in communication with a source of fluid, while a waste outlet is also attached to the casing with the waste outlet being in fluid flow communication with a waste disposal. A dialysis supply and waste management system is also disposed within the enclosure of the casing and may include a plumbing arrangement in fluid flow communication with the supply inlet at a first end of the plumbing arrangement and a connection port formed at a second end of the plumbing arrangement. In addition, a backflow preventer is in fluid flow communication with the plumbing arrangement for preventing retrograde flow of a fluid through the plumbing arrangement and a trap primer is in fluid flow communication with the plumbing arrangement.

In another embodiment, a system may include a dialysis machine in fluid flow communication with a dialysis service box. The dialysis service box may include a casing having a top side portion, a bottom side portion, a rear side portion, a left side portion and a right side portion that collectively define an enclosure. A supply inlet is attached to the casing and is in communication with a source of fluid, while a waste outlet is also attached to the casing with the waste outlet being in fluid flow communication with a waste disposal. A dialysis supply and waste management system is disposed within the enclosure of the casing and may include a plumbing arrangement in fluid flow communication with the supply inlet at a first end of the plumbing arrangement and a connection port formed at a second end of the plumbing arrangement. A backflow preventer is in fluid flow communication with the plumbing arrangement for preventing retrograde flow of a fluid through the plumbing arrangement and a trap primer in fluid flow communication with the plumbing arrangement for allowing the fluid to enter the waste outlet.

In yet another embodiment, a method of manufacturing a dialysis service box may include:
  forming a casing having a top side portion, a bottom side portion, a left side portion, an opposing right side portion, and a rear side portion for defining an enclosure;
  installing a plumbing arrangement within the enclosure of the casing in which the plumbing arrangement includes a first end having a supply inlet and a second end having a connection port configured to be in fluid flow communication with a dialysis machine;
  installing a trap primer within the enclosure of the casing and in communication with the plumbing arrangement; and
  installing a backflow preventer within the enclosure of the casing and in fluid flow communication with the plumbing arrangement.

BRIEF DESCRIPTION OF THE DRAWINGS

FIG. 5 is a front view of the dialysis service box showing the dimension of the casing that houses the dialysis supply and waste system;

FIG. 6 is a side view of the dialysis service box;

FIG. 7 is a top view of the dialysis service box; and

Corresponding reference characters indicate corresponding elements among the various views of the drawings. The headings used in the figures should not be interpreted to limit the scope of the claims.

DETAILED DESCRIPTION

As described herein, a dialysis service box and method of manufacturing and using the dialysis service box is configured and arranged to provide a centralized control and plumbing arrangement of dialysis machines. The dialysis service box can be universally installed in a convenient location to operate, control, and adjust any connected dialysis machine that requires a potable water supply connection, waste outlet connection, backflow preventer, and trap primers. In addition, a method of retrofitting the dialysis service box to one or more existing dialysis machines to optimize operation, reduce the cost of maintenance, ease the control and adjustment of the water supply and waste disposal of the dialysis machine is described.

Figure 1:
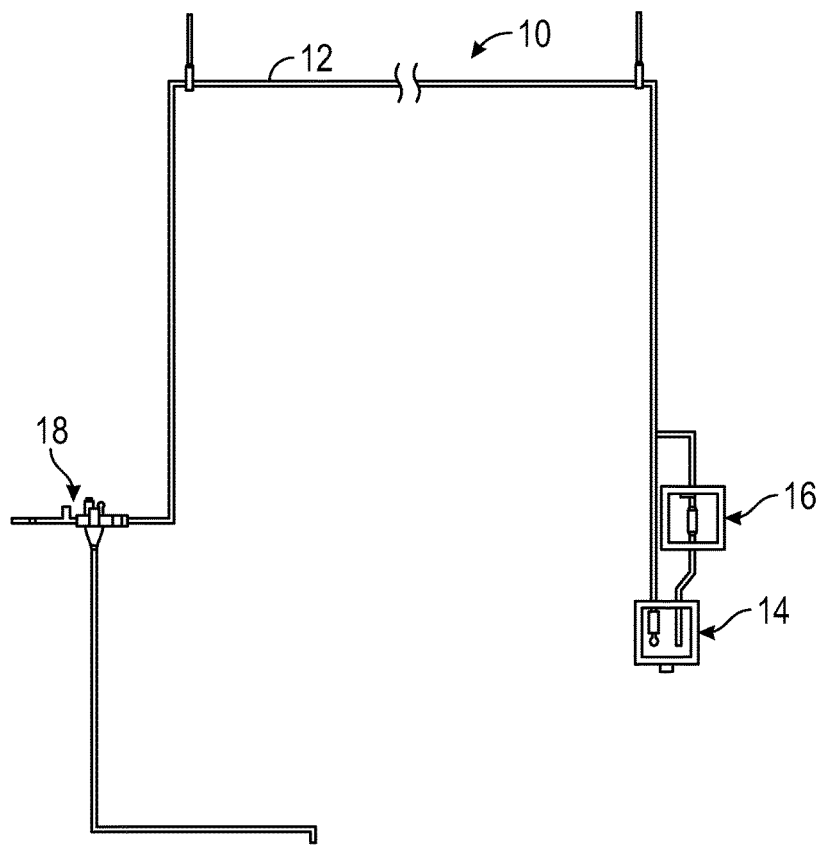
FIG. 1 is a simplified illustration showing a prior art dialysis service system.
Figure 2:
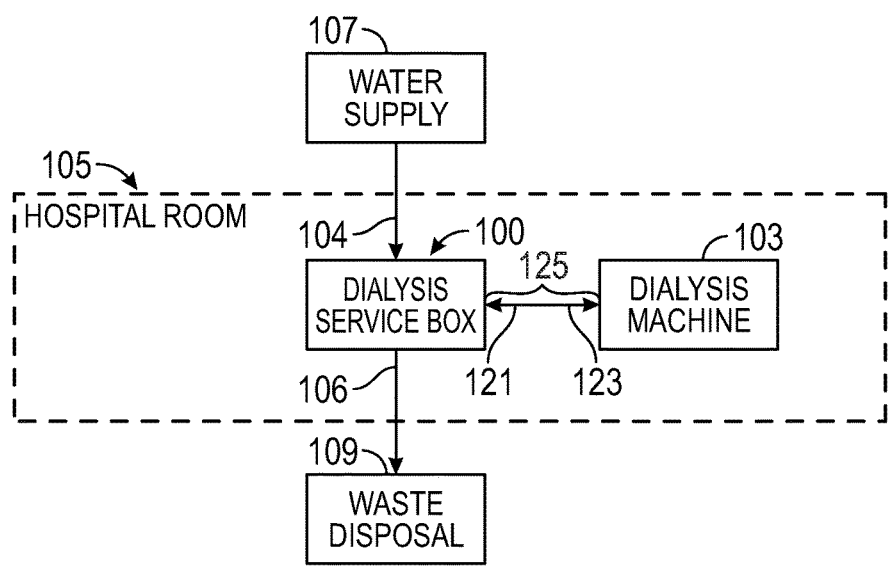
FIG. 2 is a simplified block diagram showing a dialysis service system having a dialysis service box connected to a dialysis machine in a hospital room setting.

Referring to the drawings, an embodiment of the dialysis service box is illustrated and generally indicated as 100 in FIGS. 2-8. In general, as shown in FIG. 2, the dialysis service box 100 provides a means for managing the flow of potable water from a public water supply 107 through the dialysis service box 100 and waste disposal system 109 for disposal of waste products from a dialysis machine 103 in fluid flow communication with the dialysis service box 100 via a connection conduit 125. In one embodiment, the dialysis service box 100 may be recessed within the wall of a hospital room 105 or other healthcare facility to provide convenient access for connection of the dialysis service box 100 to the dialysis machine 103; however in other embodiments the dialysis service box 100 may be wall or cabinet mounted. In operation, the dialysis service box 100 is configured to be universally installed to operate, control, and adjust any dialysis machine 103 that requires a supply connection, waste connection, reduced pressure backflow preventer, and trap priming as shall be discussed in greater detail below.

Figure 3:
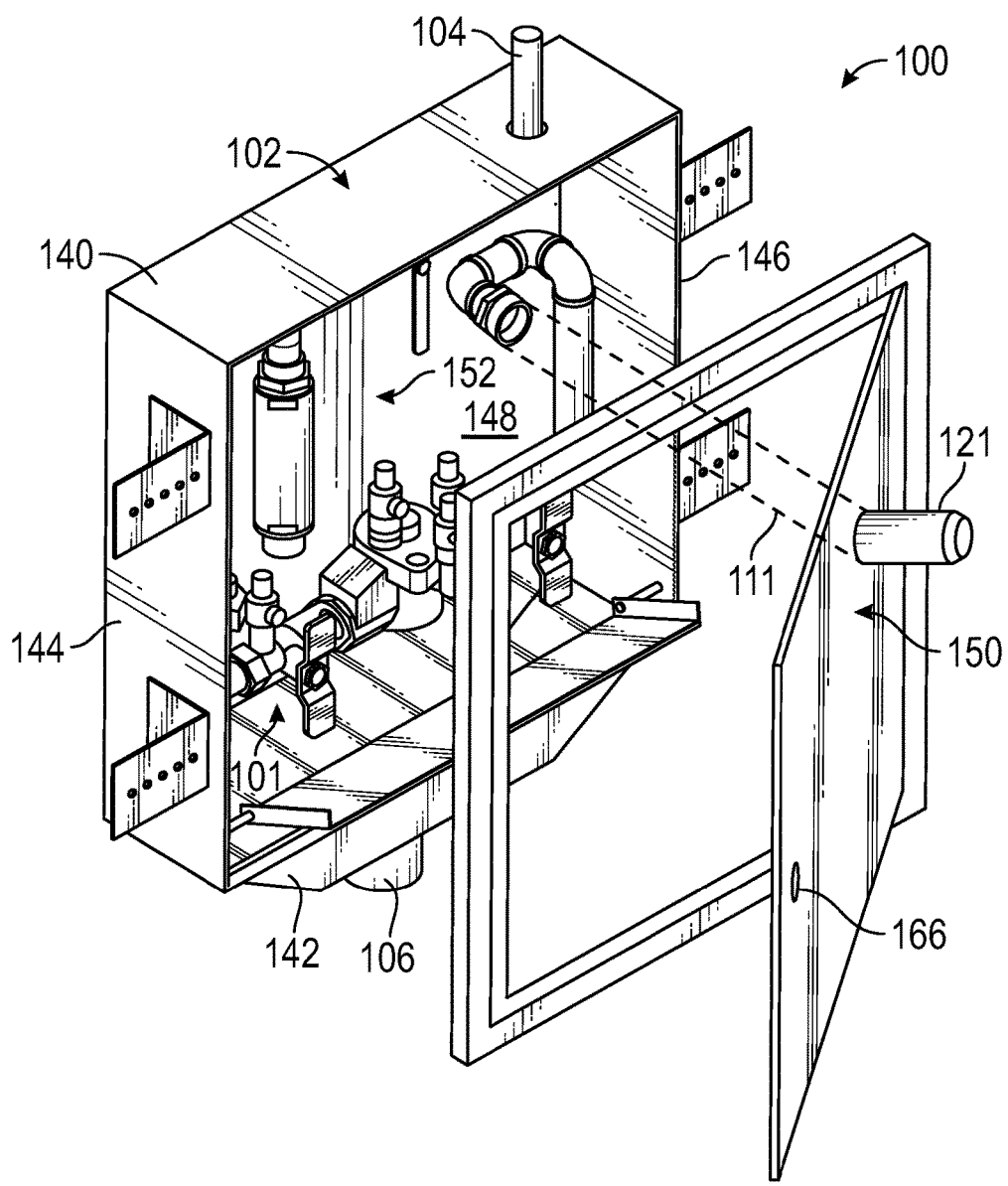
FIG. 3 is a perspective view of one embodiment of a dialysis service box.

Referring to FIG. 3, the dialysis service box 100 includes a casing 102 having a door assembly 150 that communicates with an enclosure 152 defined by the casing 102 for housing a dialysis supply and waste management system 101 having various components that manage the water supply and waste disposal operations for the dialysis machine 103. As shown, the casing 102 includes a supply inlet 104 coupled to plumbing arrangement 132 that transports a supply of water from the water supply 107, for example a public water supply system, to the dialysis service box 100 and a waste outlet 106 in communication with a fixture drain (not shown) for allowing waste received from the dialysis machine 103 to exit the dialysis service box 100 for proper disposal in the waste disposal system 109, such as a public sewer system. To facilitate fluid flow communication between the service box 100 and the dialysis machine 103, the connection port 111 may include an adapter 121, for example, a male adapter.

Referring to FIGS. 5-7, the casing 102 forms a top side portion 140, a bottom side portion 142, a left side portion 144, a right side portion 146, a rear portion 148, and a door assembly 150 that collectively define the enclosure 152 for housing the various components of the dialysis supply and waste management system 101 of the dialysis service box 100. The door assembly 150 may include a knob 166 for opening and closing the door assembly 150. In one embodiment, the casing 102 may have a generally rectangular or square-shaped configuration. For example, the casing 102 may have a length 700 of about 17 inches, a width 702 of about 17 inches, and a depth 704 of about 4 inches. In some embodiments, the dialysis service box 100 may have a length 700 between 15 to 20 inches, a width 702 between 15 to 20 inches, and a depth 704 between 2 to 6 inches. In one embodiment, the bottom side portion 142 may have a tapered configuration that channels liquids, such as water and waste, into the waste outlet 106. In some embodiments, the casing 102 may be a recessed box built with a combination of bent and welded 18 gauge stainless steel with the door assembly 150 being made from a separate pre-manufactured stainless steel. The apparatus, articles of manufacture, and methods described herein are not limited in this regard.

Figure 4:
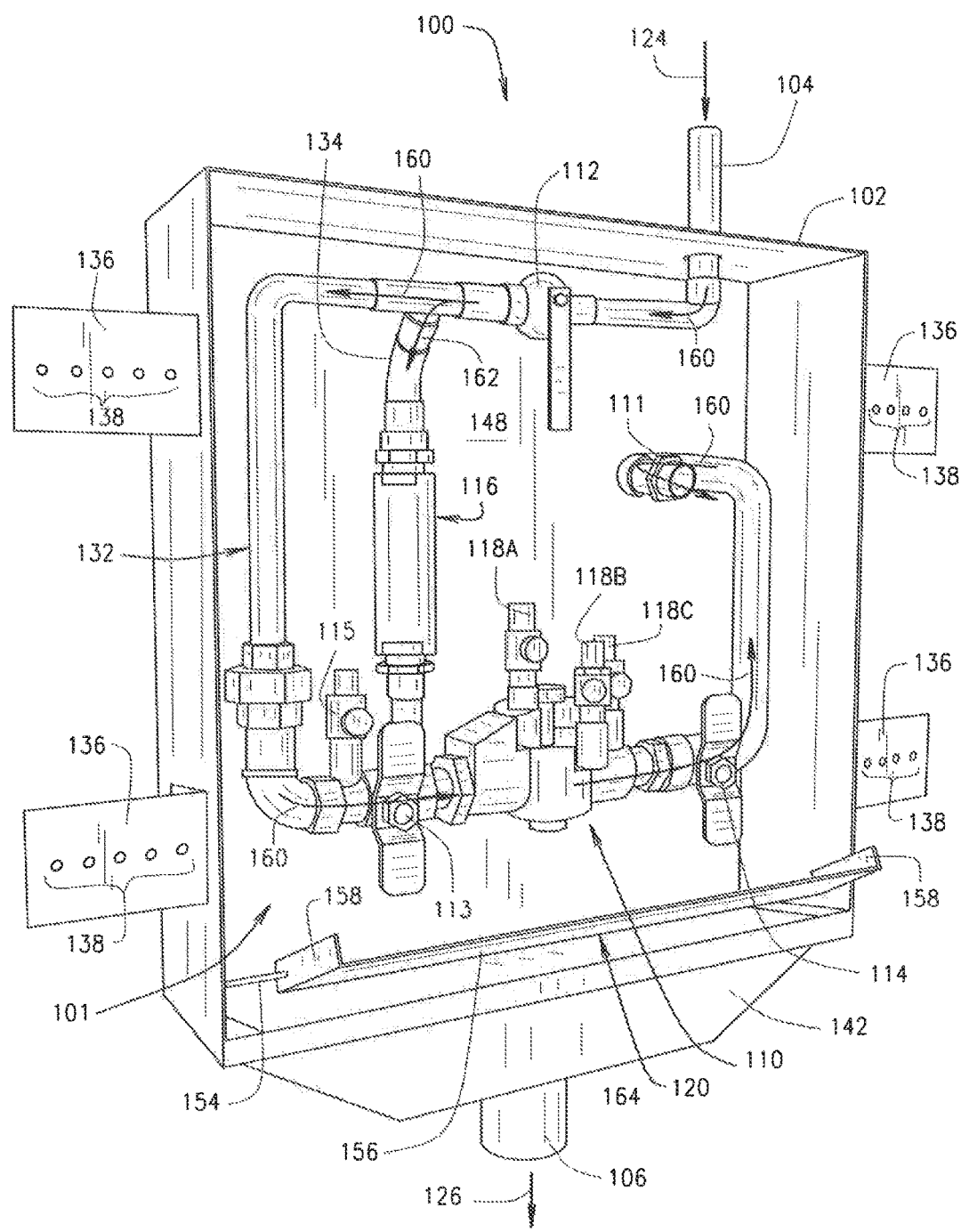
FIG. 4 is a perspective view of the dialysis service box illustrating the various components of a dialysis supply and waste system.

Referring to FIG. 4, the dialysis supply and waste management system 101 includes various components for the management of the water supply and waste disposal operations for the dialysis service box 100. In some embodiments, the dialysis supply and waste management system 101 includes a backflow preventer 110 for preventing retrograde flow of liquid back through the plumbing arrangement 132 of the dialysis supply and waste system 101, a trap primer 116 to insure periodic priming of a p-trap (not shown) that is connected to the waste outlet 106 in fluid flow communication with the waste disposal system 109 to prevent the backflow of waste gases back into the dialysis service box 100, and first, second and third shut-off valves 112, 113 and 114 for preventing fluid flow communication at various points along the plumbing arrangement 132 of the dialysis supply and waste management system 101. In some embodiments, the first, second and third shut-off valves 112, 113, and 114 may each be a ½" copper ball valve configured to permit or prevent fluid flow communication through plumbing arrangement 132 when actuated.

As noted above, the reduced pressure backflow preventer 110 prevents retrograde flow of liquid back through the plumbing arrangement 132 of the dialysis service box 100. In one embodiment, the reduced pressure backflow preventer 110 is a testable backflow preventer that falls under the UPC code requirement for most cities and municipalities to protect the potable water supply from possible contaminants generated by the dialysis machine 103 that can be caused if retrograde flow of liquids were allowed to occur. In addition, the reduced pressure backflow preventer 110 includes a dump port 164 that allow for water to exit in case of retrograde flow of liquid due to a loss of water pressure or mechanical failure of the reduced pressure backflow preventer 100. As shown, the reduced pressure backflow preventer 110 includes a plurality of test ports, designated 118A, 118B and 118C, which are configured to engage a testing device designed to test and ensure the proper operation of the reduced pressure backflow preventer 110. In one embodiment, the reduced pressure backflow preventer 110 may be a ½" WATTS 009QT RP Assembly 1, although other suitable types of reduced pressure backflow preventers may be utilized.

The trap primer 116 is in fluid flow communication with plumbing arrangement 132 for insuring periodic priming of the p-trap to prevent waste gases from flowing back into the dialysis service box 100 by allowing sufficient wetting of the p-trap by the gravity flow of water or water droplets into the p-trap through an aperture 165 (FIG. 5) formed at the lower end of the trap primer 116. In one embodiment, the trap primer 116 may be a ½ MIFAB Trap Primer 2 designed to meet UPC code requirements. In addition, the casing 102 may include a drip deflection tray 120 mounted proximate the bottom side portion 142 which is engaged between the right side portion 144 and left side portion 146 of the casing 102 and is configured to deflect any liquid that may drip from between the fittings of the plumbing arrangement 132 or other components of the dialysis supply and waste management system 101. The drip deflection tray 120 forms a tray body 156 defining opposing side walls 158 with a pair of rods 154 attached or integral with the opposing side walls 158 of the tray body 156 that are engaged to the right and left side portions 144 and 146 of the casing 102. The rods 154 of the tray body 156 are configured to swivel such that the drip deflection tray 120 may be positioned between a folded position when the door assembly 150 is closed and in an extended position to when the door assembly 150 is open to prevent spillage of liquid outside the casing 102. In one embodiment, the drip deflection tray 120 may be made from stainless steel.

As noted above, the supply inlet 104 is in fluid flow communication with the water supply 107 for providing an inflow 124 of liquid that enters a first end of the plumbing arrangement 132 for supplying water to the dialysis machine 103 through a connection port 111 located at a second end of the plumbing arrangement 132 to establish fluid flow communication. The connection port 111 may include a male adapter 121 configured to engage a female adapter 123 associated with the dialysis machine 103 via a connection conduit 125 (shown schematically in FIG. 2). As illustrated, the fluid pathway of water, designated 160, travels through the plumbing arrangement 132 of the dialysis service box 100. In addition, a portion of fluid pathway 160, designated fluid pathway 162, may be diverted to the trap primer 116 for supplying the trap primer 116 sufficient water to prime the p trap as discussed above through a second plumbing arrangement 134 coupled to the plumbing arrangement 132. A bleed port 115, for example a pressure relief valve, is in communication with the plumbing arrangement 132 to provide a means for bleeding excess pressurized water if the pressure of the water within the plumbing arrangement 132 exceeds a predetermined threshold. In some embodiments, the pressure of the water flowing through the plumbing arrangement 132 may be 80 psi, or preferably 50 psi, although the pressure of the water may range between 40-80 psi.

Referring to FIGS. 4 and 5, the casing 102 may include four mounting tabs 136 having a plurality of apertures 138 for receiving a screw, nail or other suitable means of attachment (not shown) such that the casing 102 may be secured within a recess formed inside a wall of a hospital room or mounted directly on the wall or a cabinet.

In one embodiment, the supply inlet 104 may be ½" copper type "L" tube configured to permit sufficient flow of water into the plumbing arrangement 132. The plumbing arrangement 132 may include a ½" copper tee that permits diversion of second flow pathway 162 the second plumbing arrangement 134 having a ½" copper type "L" tube that is coupled to a ½" copper female adapter engaged to the trap primer 116. In addition, a ½" copper male adapter may be engaged to the opposite end of the trap primer 116 coupled to another ½" copper type "L" tube defining aperture 165 for permitting gravity flow of liquid into the waste disposal 109.

As shown, a ½" copper type "L" tube may be coupled between the ½" copper tee and a ½" copper 90, which is engaged to another ½" copper type "L" tube. A ½" copper HP brass union is interposed between the ½" copper type "L" tube and a ½" brass street 90. In some embodiments, a ½" brass 90 may be coupled to a ½"×2½" brass nipple between the reduced pressure backflow preventer 116 and the connection port 111. Moreover, a'/Z' brass 90 may be connected between the ½"×2½" brass nipple and a ½" brass street 90, which is coupled to a ½" brass 90 for engagement with the connection port 111.

Figure 8:
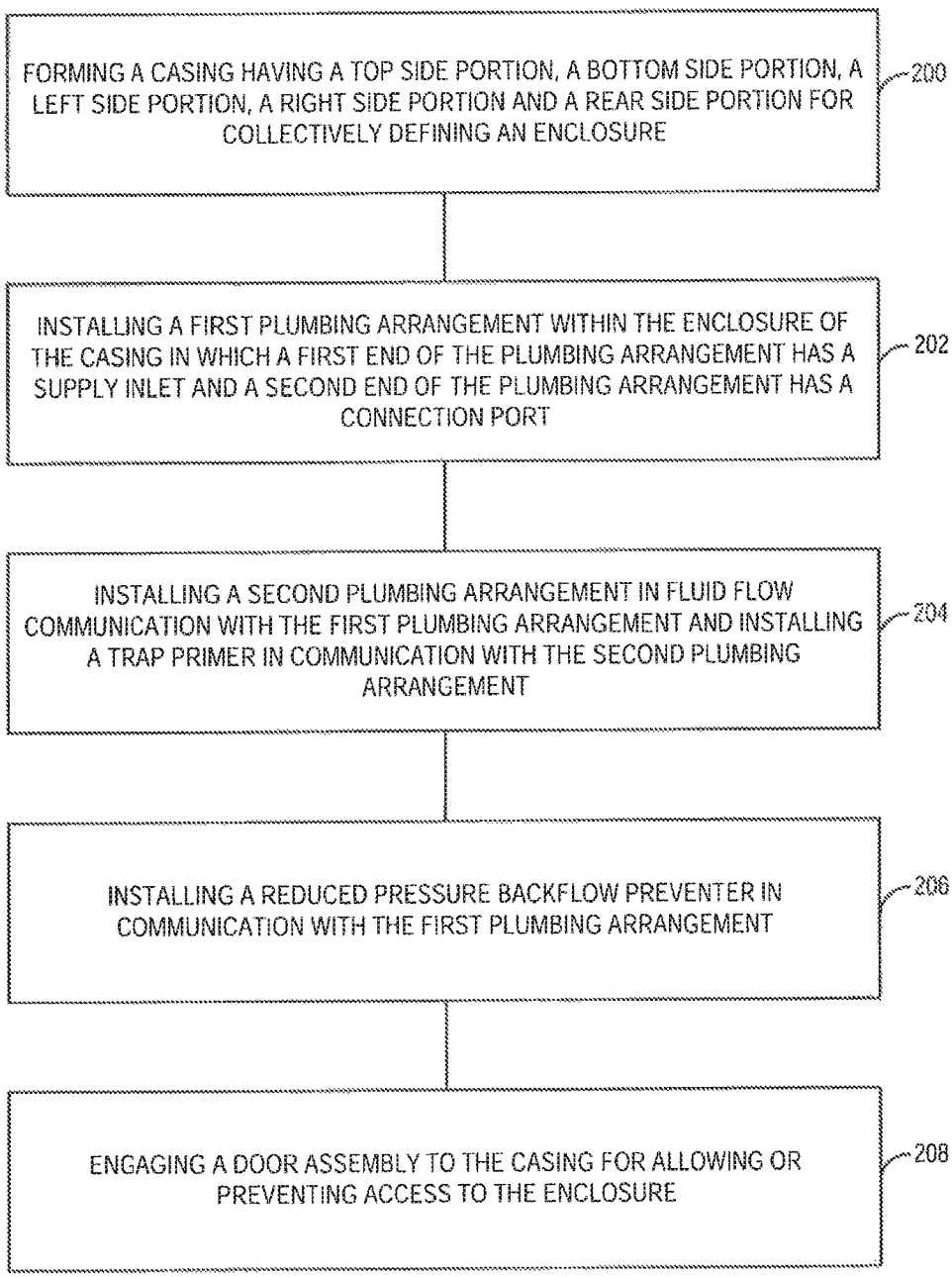
FIG. 8 is a flow chart illustrating one method for manufacturing the dialysis service box.

Referring to FIG. 8, a flow chart illustrates one method for manufacturing the dialysis service box 100. At block 200, forming the casing 102 having a top side portion 140, a bottom side portion 142, a left side portion 144, an opposing right side portion 146, and a rear portion 148 for defining an enclosure 152. At block 202, installing plumbing arrangement 132 within the enclosure 152 of the casing 102 in which one end of the plumbing arrangement 132 has a supply inlet 104 and the opposite end has a connection port 111. At block 204, installing a second plumbing arrangement 134 to the plumbing arrangement 132 and then installing a trap primer 116 in communication with the second plumbing arrangement 134. Finally, at block 206, installing a reduced pressure backflow preventer 110 in communication with the plumbing arrangement 132. At block 208, engaging a door assembly 150 to the casing 102 for allowing or preventing access to the enclosure 152.

In addition, a connection port 111 is located at a second end of the plumbing arrangement 132 to exit waste fluids from the dialysis service box 100. The connection port 111 may include a male adapter configured to engage a female adapter (not shown) of the dialysis machine 103. As illustrated, the fluid pathway of water, designated 160, travels from the thermostatic mixing component through the plumbing arrangement 132 of the dialysis service box 100. In addition, a portion of fluid pathway 160, designated fluid pathway 162, may be diverted to the trap primer 116 for supplying the trap primer 116 sufficient water to prime the p trap as discussed above through a second plumbing arrangement 134 coupled to the plumbing arrangement 132. A bleed port 115, for example a pressure relief valve, is in communication with the plumbing arrangement 132 to provide a means for bleeding excess pressurized water if the pressure of the water within the plumbing arrangement 132 exceeds a predetermined threshold. In some embodiments, the pressure of the water flowing through the plumbing arrangement 132 may be 80 psi, or preferably 50 psi, although the pressure of the water may range between 40-80 psi.

Referring back to FIGS. 4 and 5, the casing 102 may include four mounting tabs 136 having a plurality of apertures 138 for receiving a screw, nail or other suitable means of attachment (not shown) such that the casing 102 may be secured within a recess formed inside a wall of a hospital room or mounted directly on the wall or a cabinet.

In one embodiment, the warm water inlet 135 and cold water inlet 137 may both be a copper type "L" tube configured to permit sufficient flow of water into the plumbing arrangement 132. The plumbing arrangement 132 may include a copper tee that permits diversion of second flow pathway 162 the second plumbing arrangement 134 having a copper type "L" tube that is coupled to a copper female adapter engaged to the trap primer 116. In addition, a'/2" copper male adapter may be engaged to the opposite end of the trap primer 116 coupled to another copper type "L" tube defining aperture 165 for permitting gravity flow of liquid into the waste disposal 109. As shown, a copper type "L" tube may be coupled between the 'A" copper tee and a copper 90, which is engaged to another copper type "L" tube. A'/2" copper FIP brass union is interposed between the copper type "L" tube and a'/2" brass street 90. In some embodiments, a brass 90 may be coupled to a 'A"×2½" brass nipple between the reduced pressure backflow preventer 116 and the connection port 111. Moreover, a V brass 90 may be connected between the ×2½" brass nipple and a 'A" brass street 90, which is coupled to a brass 90 for engagement with the connection port 111.

Referring to FIG. 8, a flow chart illustrates one method for manufacturing the dialysis service box 100. At block 200, forming the casing 102 having a top side portion 140, a bottom side portion 142, a left side portion 144, an opposing right side portion 146, and a rear portion 148 for defining an enclosure 152. At block 202, installing a first plumbing arrangement within the enclosure of the casing in which a first end of the plumbing arrangement has a cold water inlet in communication with a source of cold water and a warm water inlet in communication with a source of warm water, and a second end of the plumbing arrangement having a connection port. At block 204, installing a thermostatic mixing component 125 in fluid flow communication with the cold water inlet and the warm water inlet. At block 206, mixing the warm water and the cold water within the thermostatic mixing component 125 to produce mixed water at a predetermined temperature between the temperature of the cold water and the temperature of the warm water. At block 208, engaging a door assembly 150 to the casing 102 for allowing or preventing access to the enclosure 152.

It should be understood from the foregoing that, while particular embodiments have been illustrated and described, various modifications can be made without departing from the spirit and scope of the invention as will be apparent to those skilled in the art. Such changes and modifications are within the scope and teachings of this invention as defined in the claims appended hereto.

What is claimed is:

1. A dialysis service box comprising:
    a casing having a top side portion, a bottom side portion, a rear side portion, a left side portion and a right side portion that collectively define an enclosure;
    a supply inlet configured to communicate with a source of fluid;
    a waste outlet configured to communicate with a waste disposal; and
    a dialysis supply and waste management system disposed within the enclosure of the casing, the dialysis supply and waste management system comprising:
        a plumbing system in fluid flow communication with the supply inlet;
        a connection port configured to provide fluid to a dialysis machine;
        a backflow preventer in fluid flow communication with the plumbing system and configured to prevent retrograde fluid flow through the plumbing arrangement; and
        a trap primer in fluid flow communication with the plumbing arrangement and configured for delivering priming fluid to the waste outlet by gravity flow;
    the dialysis service box further comprising a first adapter associated with the connection port, the first adapter configured to supply fluid to the dialysis machine.

2. The dialysis service box of claim 1, wherein the first adapter is disposed proximate an outside surface of the casing.

3. The dialysis service box of claim 2, wherein the outside surface of the casing comprises one of the top side portion, the bottom side portion, the rear side portion, the left side portion, and the right side portion.

4. The dialysis service box of claim 2, wherein the casing further includes a door assembly, and further wherein the first adapter is disposed proximate an outside surface of the door assembly.

5. The dialysis service box of claim 4, wherein the first adapter is connected to an outside surface of the door assembly.

6. The dialysis service box of claim 1, wherein the first adapter is configured for fluid communication with a second adapter associated with the dialysis machine.

7. The dialysis service box of claim 6, wherein the first adapter comprises a male adapter and the second adapter comprises a female adapter.

8. The dialysis service box of claim 6, further comprising a fluid conduit extending between the casing and the dialysis machine, wherein the first adapter is configured to connect to a first end of the fluid conduit proximate the casing, and the second adapter is configured to connect to a second end of the fluid conduit proximate the dialysis machine.

9. The dialysis service box of claim 1, wherein the connection port comprises the first adapter.

10. A system comprising:
    a dialysis machine;
    a dialysis service box in fluid flow communication with the dialysis machine, the dialysis service box comprising:
        a casing defining an enclosure having a top side portion, a bottom side portion, a rear side portion, a left side portion and a right side portion that collectively define an enclosure,
        a supply inlet in fluid flow communication with a source of fluid;
        a waste outlet in fluid flow communication with a waste disposal; and
        a dialysis supply and waste management system disposed within the enclosure of the casing, the dialysis supply and waste management system comprising:
            a plumbing arrangement in fluid flow communication with the supply inlet and having a connection port configured for fluid communication with the dialysis machine;
            a backflow preventer in fluid flow communication with the plumbing arrangement for preventing retrograde fluid flow a through the plumbing arrangement; and
            a trap primer in fluid flow communication with the plumbing arrangement and configured for delivering priming fluid to the waste outlet by gravity flow;
        the dialysis service box further comprising a first adapter associated with the connection port and configured to supply fluid to the dialysis machine.

11. The dialysis service box of claim 10, wherein the first adapter is disposed proximate an outside surface of the casing.

12. The dialysis service box of claim 10, wherein the first adapter is configured for fluid communication with a second adapter associated with the dialysis machine.

13. The dialysis service box of claim 12, wherein the first adapter comprises a male adapter and the second adapter comprises a female adapter.

14. The dialysis service box of claim 12, further comprising a fluid conduit extending between the casing and the dialysis machine, wherein the first adapter is configured to connect to a first end of the fluid conduit proximate the casing, and the second adapter is configured to connect to a second end of the fluid conduit proximate the dialysis machine.

15. The dialysis service box of claim 10, wherein the outside surface of the casing comprises one of the top side portion, the bottom side portion, the rear side portion, the left side portion, and the right side portion.

16. The dialysis service box of claim 10, wherein the casing further includes a door assembly, and further wherein the first adapter is disposed proximate an outside surface of the door assembly.

17. The dialysis service box of claim 16, wherein the first adapter is connected to an outside surface of the door assembly.

18. The dialysis service box of claim 10, wherein the connection port comprises the first adapter.

19. A method of manufacturing a dialysis service box comprising:
  forming a casing having a top side portion, a bottom side portion, a left side portion, an opposing right side portion, and a rear side portion defining an enclosure and including a waste outlet;
  installing a plumbing arrangement within the enclosure, the plumbing arrangement including a supply inlet and a connection port configured to be in fluid flow communication with a dialysis machine;
  installing a trap primer within the enclosure and in communication with the plumbing arrangement and the waste outlet for delivering priming fluid to the waste outlet by gravity flow;
  installing a backflow preventer within the enclosure and in fluid flow communication with the plumbing arrangement; and
  attaching a first adapter to the connection port and configuring the first adapter to supply fluid to the dialysis machine.

20. The method of claim 19, wherein the casing further includes a door, the method further comprising attaching the first adapter to an outside surface of the casing.

* * * * *